US011756663B2

(12) United States Patent
Neumann

(10) Patent No.: US 11,756,663 B2
(45) Date of Patent: Sep. 12, 2023

(54) METHOD OF AND SYSTEM FOR DETERMINING A PRIORITIZED INSTRUCTION SET FOR A USER

(71) Applicant: KPN INNOVATIONS, LLC., Lakewood, CO (US)

(72) Inventor: Kenneth Neumann, Lakewood, CO (US)

(73) Assignee: KPN INNOVATIONS, LLC., Lakewood, CO (US)

( * ) Notice: Subject to any disclaimer, the term of this patent is extended or adjusted under 35 U.S.C. 154(b) by 364 days.

(21) Appl. No.: 16/939,230

(22) Filed: Jul. 27, 2020

(65) Prior Publication Data

US 2022/0028517 A1 Jan. 27, 2022

(51) Int. Cl.
*G16H 20/30* (2018.01)
*G16H 50/30* (2018.01)
*G16H 20/60* (2018.01)
*G06N 20/20* (2019.01)

(52) U.S. Cl.
CPC ............. *G16H 20/30* (2018.01); *G06N 20/20* (2019.01); *G16H 20/60* (2018.01); *G16H 50/30* (2018.01)

(58) Field of Classification Search
CPC ......... G16H 10/00–80/00; G06N 3/00–99/007
See application file for complete search history.

(56) References Cited

U.S. PATENT DOCUMENTS

| 8,200,548 | B2 | 6/2012 | Wiedl |
| 9,805,163 | B1 * | 10/2017 | Ranch ................... G16H 10/60 |
| 10,026,055 | B2 | 7/2018 | Riel-Dalpe et al. |
| 10,130,311 | B1 * | 11/2018 | De Sapio ............. A61B 5/7455 |
| 11,094,016 | B1 * | 8/2021 | Welz ....................... H04L 67/75 |
| 2002/0004749 | A1 | 1/2002 | Froseth et al. |
| 2004/0210621 | A1 | 10/2004 | Antonellis |

(Continued)

FOREIGN PATENT DOCUMENTS

| EP | 3272280 A1 * | 1/2018 | ........... A61B 5/0075 |
| WO | WO-2005013174 A2 * | 2/2005 | ......... G06F 19/3475 |

OTHER PUBLICATIONS https://www.sciencedirect.com/science/article/pii/S0959652620306740.
https://www.semanticscholar.org/paper/The-Meal-Delivery-Routing-Problem-Reyes-Erera/1c0b0f117437f4123cdeb77c24210610733de706.

*Primary Examiner* — Jonathon A. Szumny
(74) *Attorney, Agent, or Firm* — CALDWELL INTELLECTUAL PROPERTY LAW

(57) ABSTRACT

A system for determining a prioritized instruction set for a user, the system comprising a computing device, wherein the computing device is configured to receive at least a physiological goal and provide a plurality of biological extraction data. Computing device may determine a user baseline profile using training data, wherein training data correlates biological extraction data and physiological goals to baseline profile elements, train a machine-learning model using the training data, and determine the user baseline profile as a function of the machine-learning model. Computing device may generate a differential action as a function of the user baseline profile and the physiological goal, receive a plurality of user preference data, and selecting the differential action from the plurality of candidate differential actions. Computing device may receive an updated biological extraction datum corresponding to the user and may modify the differential action as a function of the updated biological extraction datum.

20 Claims, 8 Drawing Sheets

(56) References Cited

U.S. PATENT DOCUMENTS

| | | |
|---|---|---|
| 2010/0280895 A1 | 11/2010 | Mottola |
| 2011/0093249 A1* | 4/2011 | Holmes .................. G16H 50/50 |
| | | 703/6 |
| 2014/0058794 A1 | 2/2014 | Malov et al. |
| 2014/0255882 A1* | 9/2014 | Hadad ................ G09B 19/0092 |
| | | 434/127 |
| 2015/0227888 A1 | 8/2015 | Levanon et al. |
| 2016/0372005 A1 | 12/2016 | Bajpai et al. |
| 2017/0024789 A1 | 1/2017 | Frehn et al. |
| 2017/0372197 A1 | 12/2017 | Baughman et al. |
| 2018/0060494 A1* | 3/2018 | Dias ....................... G16H 70/20 |
| 2018/0075219 A1* | 3/2018 | Klein ..................... G16H 20/70 |
| 2018/0293638 A1 | 10/2018 | Simpson |
| 2018/0308066 A1 | 10/2018 | Hadatsuki et al. |
| 2019/0043143 A1 | 2/2019 | Camacho et al. |
| 2019/0065687 A1* | 2/2019 | Mei ........................ A61B 34/10 |
| 2019/0198149 A1* | 6/2019 | Bastide .................. G16H 20/30 |
| 2019/0317998 A1* | 10/2019 | Komine ................. G06N 20/00 |
| 2019/0336824 A1* | 11/2019 | Fung .................. A63B 22/0285 |
| 2019/0355454 A1* | 11/2019 | Deshpande ............ G16H 40/67 |
| 2020/0065892 A1 | 2/2020 | Brown |
| 2020/0170549 A1* | 6/2020 | Baykaner ............... G16H 10/60 |
| 2020/0250508 A1* | 8/2020 | De Magalhaes ....... G16H 15/00 |
| 2021/0406025 A1* | 12/2021 | Neumann .............. G16H 50/20 |

\* cited by examiner

METHOD OF AND SYSTEM FOR DETERMINING A PRIORITIZED INSTRUCTION SET FOR A USER

FIELD OF THE INVENTION

The present invention generally relates to the field of solution optimization. In particular, the present invention is directed to determining a prioritized instruction set for a user.

BACKGROUND

Machine-learning methods are increasingly valuable for analysis of patterns in large quantities of data. However, where the data is large and varied enough, determining a prioritized instruction set for users from machine-learning outputs can become untenable, especially with tradeoffs between sophistication and efficiency.

SUMMARY OF THE DISCLOSURE

In an aspect, a system for determining a prioritized instruction set for a user, the system comprising a computing device, wherein the computing device is designed and configured to receive, from a user, at least a physiological goal, and provide a plurality of biological extraction data corresponding to the user. Computing device may determine a user baseline profile, wherein determining the user baseline profile further comprises receiving training data including data entries, each data entry correlating biological extraction data and physiological goals to baseline profile elements, training a machine-learning model as a function of the training data; and determining the user baseline profile as a function of the machine-learning model, the plurality of biological extraction data and the at least a physiological goal. Computing device may generate a differential action as a function of the user baseline profile and the at least a physiological goal, wherein generating the differential action further comprises generating a plurality of candidate differential actions as a function of the user baseline profile and the physiological goal, receiving a plurality of user preference data; and selecting the differential action from the plurality of candidate differential actions as a function of the user preference data and the at least a physiological goal. Computing device may receive an updated biological extraction datum corresponding to the user. Computing device may modify the differential action as a function of the updated biological extraction datum.

In another aspect a method for determining a prioritized instruction set for a user, the system comprising a computing device, wherein the computing device is designed and configured to receive, from a user, at least a physiological goal, and provide a plurality of biological extraction data corresponding to the user. Computing device may determine a user baseline profile, wherein determining the user baseline profile further comprises receiving training data including data entries, each data entry correlating biological extraction data and physiological goals to baseline profile elements, training a machine-learning model as a function of the training data; and determining the user baseline profile as a function of the machine-learning model, the plurality of biological extraction data and the at least a physiological goal. Computing device may generate a differential action as a function of the user baseline profile and the at least a physiological goal, wherein generating the differential action further comprises generating a plurality of candidate differential actions as a function of the user baseline profile and the physiological goal, receiving a plurality of user preference data; and selecting the differential action from the plurality of candidate differential actions as a function of the user preference data and the at least a physiological goal. Computing device may receive an updated biological extraction datum corresponding to the user. Computing device may modify the differential action as a function of the updated biological extraction datum.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for determining a prioritized instruction set for a user. In an embodiment, a system may include a computing device, wherein the computing device is designed and configured to receive, from a user, at least a physiological goal, and provide a plurality of biological extraction data corresponding to the user. Computing device may determine a user baseline profile, wherein determining the user baseline profile further comprises receiving training data including data entries, each data entry correlating biological extraction data and physiological goals to baseline profile elements, training a machine-learning model as a function of the training data; and determining the user baseline profile as a function of the machine-learning model, the plurality of biological extraction data and the at least a physiological goal. Computing device may generate a differential action as a function of the user baseline profile and the at least a physiological goal, wherein generating the differential action further comprises generating a plurality of candidate differential actions as a function of the user baseline profile and the physiological goal, receiving a plurality of user preference data; and selecting the differential action from the plurality of candidate differential actions as a function of the user preference data and the at least a physiological goal. Computing device may receive an updated biological extraction datum corresponding to the user. Computing device may modify the differential action as a function of the updated biological extraction datum.

Figure 1:
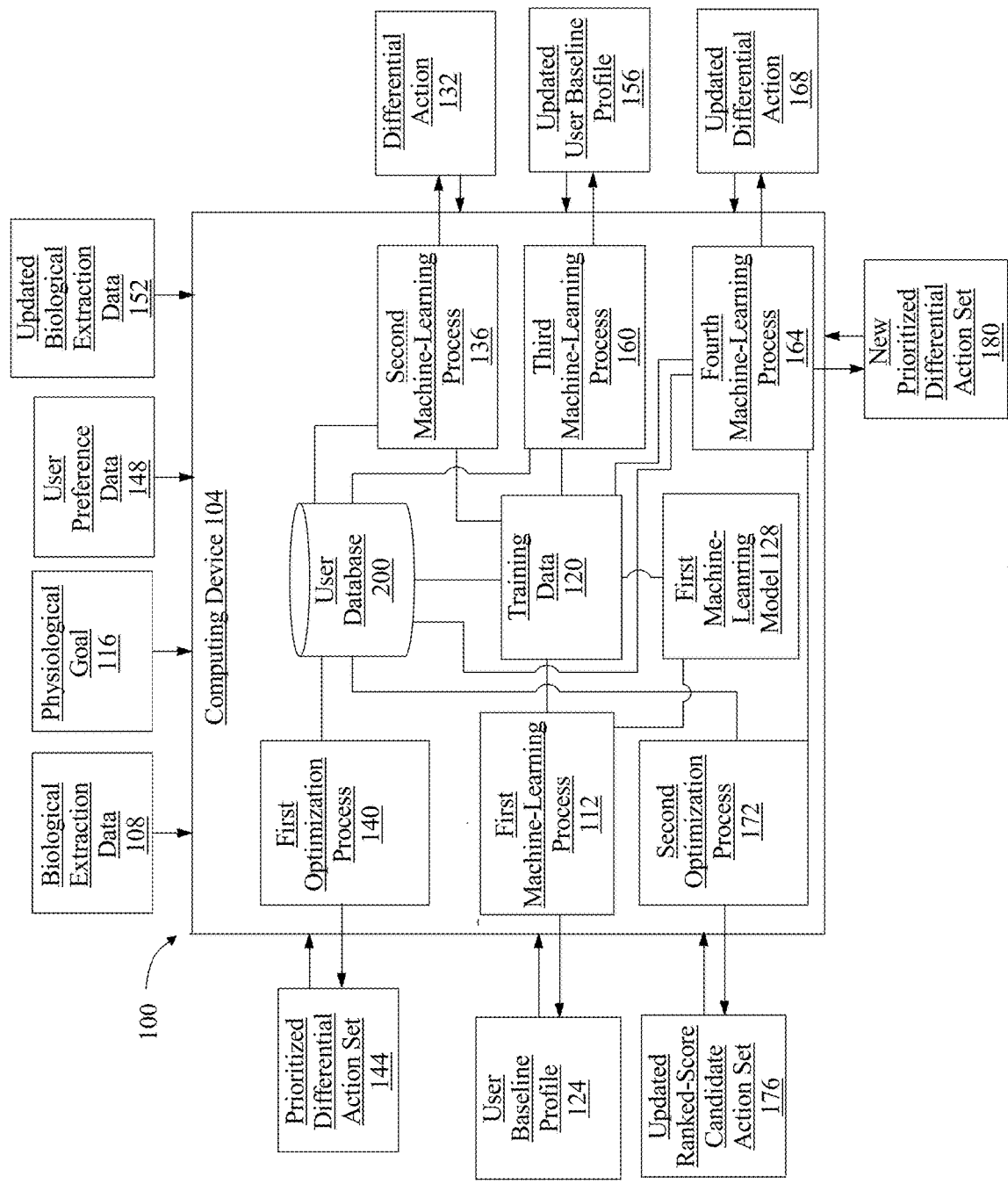
FIG. 1 is a block diagram illustrating an exemplary embodiment of a system for determining a prioritized instruction set for a user.

Referring now to FIG. 1, an exemplary embodiment of a system 100 for determining a prioritized instruction set for a user is illustrated. System includes a computing device 104 Computing device 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device.

Continuing to refer to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With further reference to FIG. 1, computing device is designed and configured to receive, from a user, at least a physiological goal. A "physiological goal," as used in this disclosure, is a desired change in a physiological state of a user, as it relates to a user baseline profile, as described in further detail below. Computing device 104 may be configured to determine physiological state of a user as a function of a biological extraction as described in further detail below. Biological extraction data 108 as used herein may include, for instance, data used as a biological extraction as described in U.S. Nonprovisional application Ser. No. 16/502,835, filed on Jul. 3, 2019, and entitled "METHODS AND SYSTEMS FOR ACHIEVING VIBRANT CONSTITUTION BASED ON USER INPUTS," the entirety of which is incorporated herein by reference.

Figure 2:
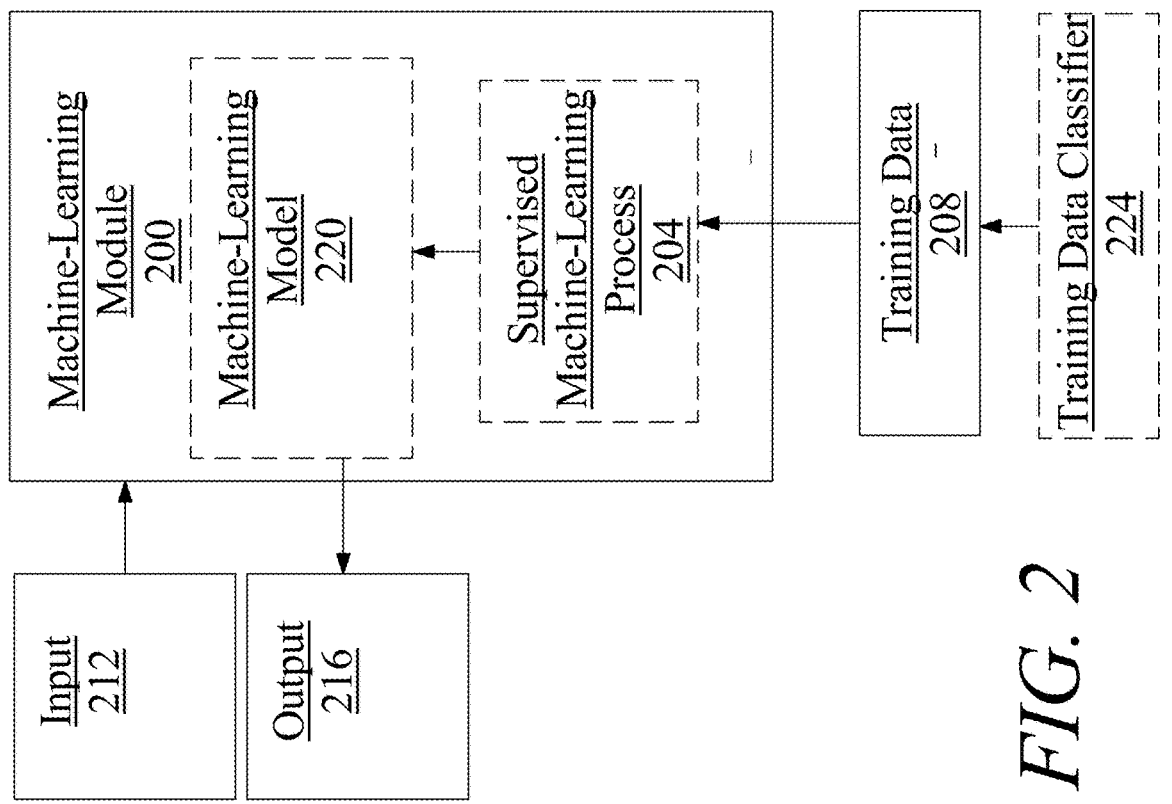
FIG. 2 is a block diagram illustrating an exemplary embodiment of a machine-learning module.

Referring now to FIG. 2, an exemplary embodiment of a machine learning module 200 is illustrated. Machine learning module 200 may refer to any machine-learning process, or plurality of machine-learning processes, used by computing device 104, for instance a first machine-learning process 112. A machine-learning module 200 may include at least a supervised machine-learning process 204. Supervised machine-learning processes 204, as defined herein, include algorithms that receive a training set 208 relating a number of inputs 212 to a number of outputs 216, and seek to find one or more mathematical relations relating inputs 212 to outputs 216, where each of the one or more mathematical relations is optimal according to some criterion specified to the algorithm using some scoring function. For instance, a supervised learning algorithm 204 may include a plurality of goals as described above as inputs 212, a plurality of instructions to address the goals as outputs 216, and a scoring function representing a desired form of relationship to be detected between inputs 212 and outputs 216; scoring function may, for instance, seek to maximize the probability that a given input and/or combination of elements inputs 212 is associated with a given output 216 to minimize the probability that a given input 212 is not associated with a given output 216. Scoring function may be expressed as a risk function representing an "expected loss" of an algorithm relating inputs 212 to outputs 216, where loss is computed as an error function representing a degree to which a prediction generated by the relation is incorrect when compared to a given input-output pair provided in training data. Persons skilled in the art, upon reviewing the entirety of this disclosure, will be aware of various possible variations of supervised machine-learning algorithms that may be used to determine relation between inputs and outputs.

Continuing in reference to FIG. 2, supervised machine-learning processes 204 may include classification algorithms, defined as processes whereby at least a computing device 104 derives, from training data, a machine-learning model 220 for sorting inputs into categories or bins of data. Classification may be performed by a classification process using, without limitation, linear classifiers such as without limitation logistic regression and/or naive Bayes classifiers, regression algorithms, nearest neighbor classifiers, support vector machines, decision trees, boosted trees, random forest classifiers, and/or neural network-based classifiers, such as supervised neural net algorithms. Supervised machine-learning processes may include, without limitation, machine-learning processes as described in U.S. Nonprovisional application Ser. No. 16/520,835, filed on Jul. 3, 2019, and entitled "METHODS AND SYSTEMS FOR ACHIEVING VIBRANT CONSTITUTION BASED ON USER INPUTS," the entirety of which is incorporated herein by reference.

Continuing in reference to FIG. 2, a training set 208 may refer to a series of "training data," as used herein, which is data containing correlations that a machine-learning process may use to model relationships between two or more categories of data elements. For instance, and without limitation, training data 120 may include a plurality of data entries, each entry representing a set of data elements that were recorded, received, and/or generated together; data elements may be correlated by shared existence in a given data entry, by proximity in a given data entry, or the like. Multiple data entries in training data 120 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 120 according to various correlations; correlations may indicate causative and/or predictive links between categories of data elements, which may be modeled as relationships such as mathematical relationships by machine-learning processes as described in further detail below. Training data 120 may be formatted and/or organized by categories of data elements, for instance by associating data elements with one or more descriptors corresponding to categories of data elements. As a non-limiting example, training data 120 may include data entered in standardized forms by persons or processes, such that entry of a given data element in a given field in a form may be mapped to one or more descriptors of categories. Elements in training data 120 may be linked to descriptors of categories by tags, tokens, or other data elements; for instance, and without limitation, training data 102 may be provided in fixed-length formats, formats linking positions of data to categories such as comma-separated value (CSV) formats and/or self-describing formats such as extensible markup language (XML), enabling processes or devices to detect categories of data. A training set 208 may be provided by a training data classifier 224 describing a subset, or subsets, of data as it relates to a category, as described above.

Alternatively or additionally, training data 120 may include one or more elements that are not categorized; that is, training data 120 may not be formatted or contain descriptors for some elements of data. Machine-learning algorithms and/or other processes may sort training data 120 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 120 to be made applicable for two or more distinct machine-learning algorithms as described in further detail below. Training data 102 used by computing device 104 may correlate any input data as described in this disclosure to any output data as described in this disclosure. Training data may contain entries, each of which correlates a machine-learning process input to a machine-learning process output, for instance without limitation, one or more elements of biological extraction data to a taste index. Training data may be obtained from previous iterations of machine-learning processes, user inputs, and/or expert inputs.

Continuing in reference to FIG. 1, computing device 104 may be configured to determine a user baseline profile 124 training first machine-learning process 112 as a function of the training data 120. Training data 120 may refer to at least an element of biological extraction data 108. Training data 120 may correspond to a subset of data, classified using a classification process for training a first machine-learning process 112. Training data 120 may be generated using a classifier generated by a classification process, as described above.

Referring now to FIG. 1, a machine-learning module 200 using a first training set 208 may refer to using a first machine-learning process 112 trained with training data 120 to generate a first machine-learning model 128. A first machine-learning model 128 may be used with a first machine-learning process 112 for generating the at least a user baseline profile 124, wherein a first machine-learning process 122 may accept an input of user biological extraction data 108 and an input of at least an element of data retrieved from a database, and a first machine-learning model 128 to generate a user baseline profile 124 as an output. In non-limiting illustrative examples, a first machine-learning model 112 may represent a mathematical model describing the tractability of a physiological goal of 'lowering blood pressure,' as a function of user biological extraction data 108 as it pertains to the user's current blood pressure, including diet, genetics, lifestyle, demographic, fitness, and the like. In further non-limiting illustrative examples, such a first machine-learning model 128 may be used by a first machine-learning process 112 with an input of user biological extraction data 108, and a function, numerical value, matrix, vector, heuristic, or similar quantitative and/or qualitative relationship correlating biological extraction data to a user baseline profile, retrieved from an online repository, published research, database, or the like, to output a user baseline profile. A 'user baseline profile," as described in this disclosure refers to a graphical output of a summation of user biological extraction data 108, including any relationships between elements of data, including any mathematical, causative, correlational relationships, or the like, between elements of data as it pertains to a user's baseline health, including current diseases, potential risks, diagnoses, addictions, proclivities, tendencies, or the like. In non-limiting illustrative examples, a user baseline profile 124 may capture all mathematical relationships between a user's baseline health, the provided biological extraction data 108, an at least a physiological goal. In further non-limiting illustrative examples, a user baseline profile may describe a pattern of sleep behavior of a user related to level of exercise and/or fitness of a user to model a user's tendency for overtraining as a potential obstacle in achieving a physiological goal, and how overtraining may manifest is other user biological extraction data 108, for instance with blood pressure, visceral fat, irritability, etc. A user baseline profile 124 and/or any machine-learning models, classifiers, subsets of data, including biological user data 108, other user baseline profiles 124, machine-learning processes, and the like may be stored and/or retrieved from a database, as described in further detail below.

Figure 3:
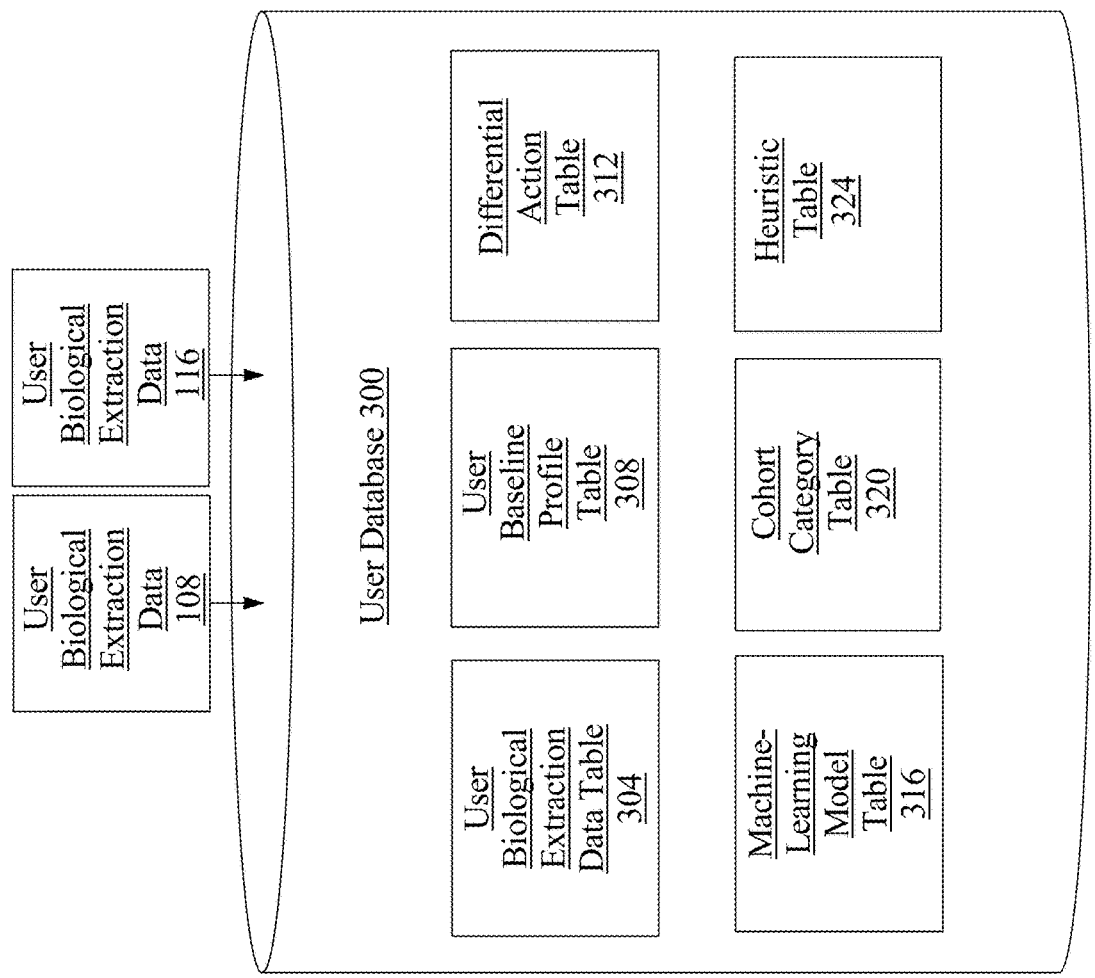
FIG. 3 is a block diagram illustrating an exemplary embodiment of a user database.

Referring now to FIG. 3, a non-limiting exemplary embodiment of a user database 300 is illustrated. Database may refer to a "user database" which at least a computing device 104 may, alternatively or additionally, store and/or retrieve data from a user biological extraction table 304, user baseline profile table 308, differential action table 312, machine-learning model table 316, cohort category table 320, and/or heuristic table 324. Determinations by a machine-learning process may also be stored and/or retrieved from the user database 120, for instance in non-limiting examples a classifier describing a subset of data, a machine-learning model that was trained using training data, and/or training data. As a non-limiting example, user database 120 may organize data according to one or more instruction tables. One or more user database 120 tables may be linked to one another by, for instance in a non-limiting example, common column values. For instance, a common column between two tables of user database 300 may include an identifier of a submission, such as a form entry, textual submission, research paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which data from one or more tables may be linked and/or related to data in one or more other tables.

Still referring to FIG. 3, in a non-limiting embodiment, one or more tables of a user database 300 may include, as a non-limiting example, a user biological extraction data table 304, which may include biological extraction analyses for use in predicting goals of a user and/or differential actions for a user and/or correlating user data to other users, entries indicating degrees of relevance to and/or efficacy in predicting a goal of a user, and/or other elements of data computing device 104 and/or system 100 may use to determine usefulness and/or relevance of user data in determining goals, instructions, and/or changes in goals and/or instructions as described in this disclosure. One or more tables may include a user baseline table 308, which may correlate user data, goals, outcomes, models, heuristics, and/or combinations thereof to one or more measures of a in achieving a goal, and/or relationships to a physiological goal. One or more tables may include, without limitation, a differential action table 312 which may contain one or more inputs identifying one or more categories of data, for instance numerical values describing the propensity of a user to follow a differential action, or the long-term effect a differential action has on future physiological goals. One or more tables may include, without limitation, a machine-learning model table 316 which may contain one or more models generated from a machine-learning process and training data. One or more tables may include, without limitation, a cohort category table 320 which may contain one or more inputs identifying one or more categories of data, for instance demographic data, physiological data, sleep pattern data, spending data, or the like, with regard to which users having matching or similar data may be expected to have similar goals and/or instruction sets as a result of optimization program output elements and/or other user data input elements. One or more tables may include, without limitation, a heuristic table 324 which may include one or more inputs describing potential mathematical relationships between at least an element of user data and goals, instructions, and rankings thereof, change in goals and/or instructions over time, and/or scoring functions for determining a rank-ordered set of goals and/or instructions, as described in further detail below.

Continuing in reference to FIG. 1, computing device 104 may generate a plurality of differential actions 132 using a second machine-learning 136 process to calculate a difference between a physiological goal 116 and a user baseline profile 124, and may retrieve from a database, a candidate differential action 132 to address a difference between a physiological goal 116 and a user baseline profile 124. A "differential action," as described in this disclosure refers to any action prescribed to a user to work towards achieving a physiological goal 116. Generating a differential action 132 may include using a second machine-learning process 136 to calculate a difference between an element of a physiological goal 116 and an element of a user baseline 124. A second machine-learning process 136 may refer to a machine-learning module 200, as described above. In non-limiting illustrative examples, a second machine-learning process 136 may include using a training set 208 including training data 120, wherein training data 120 may be data corresponding to a user baseline profile 124, a physiological goal 116, a plurality of differential actions 132, and the like. In further non-limiting illustrative examples, a second machine-leaning process 136 may use training data 120 that is identified by a classifier, and/or may refer to a data that corresponds to a second user. A second machine-learning process 136 may accept an input of at least a physiological goal 116 and a user baseline 124 to generate at least a differential action 132, of a plurality of candidate differential actions. A second machine-learning process 136 may generate a differential action 132 by retrieving an element of data from a user database 200 as it correlates to achieving a physiological goal 116 as a function of the user baseline profile 124; for instance and without limitation, this may be a query for options in addressing a physiological goal 116, with a mathematical function, matrix, vector, numerical value, or the like, that applies the user baseline profile 124 to the retrieved options. For instance in non-limiting examples, a second machine-learning process 136 may query a database for a plurality of candidate differential actions 132 in addressing a physiologic goal 116 of 'reducing blood pressure into a healthy range,' wherein candidate differential actions 132 retrieved from a database may depend on current user blood pressure, and the healthy range is for a particular user. In further non-limiting illustrative examples, a second machine-learning process 136 may use a mathematical function to compare the current user blood pressure, among other factors, to the queried 'healthy blood pressure range' according to the user baseline profile 124 to determine the efficacy of candidate differential actions 132, for instance a therapeutic dose of a blood pressure medicine, a new diet, lowering caffeine, sodium, and/or alcohol intake, and/or meditation techniques.

Figure 4:
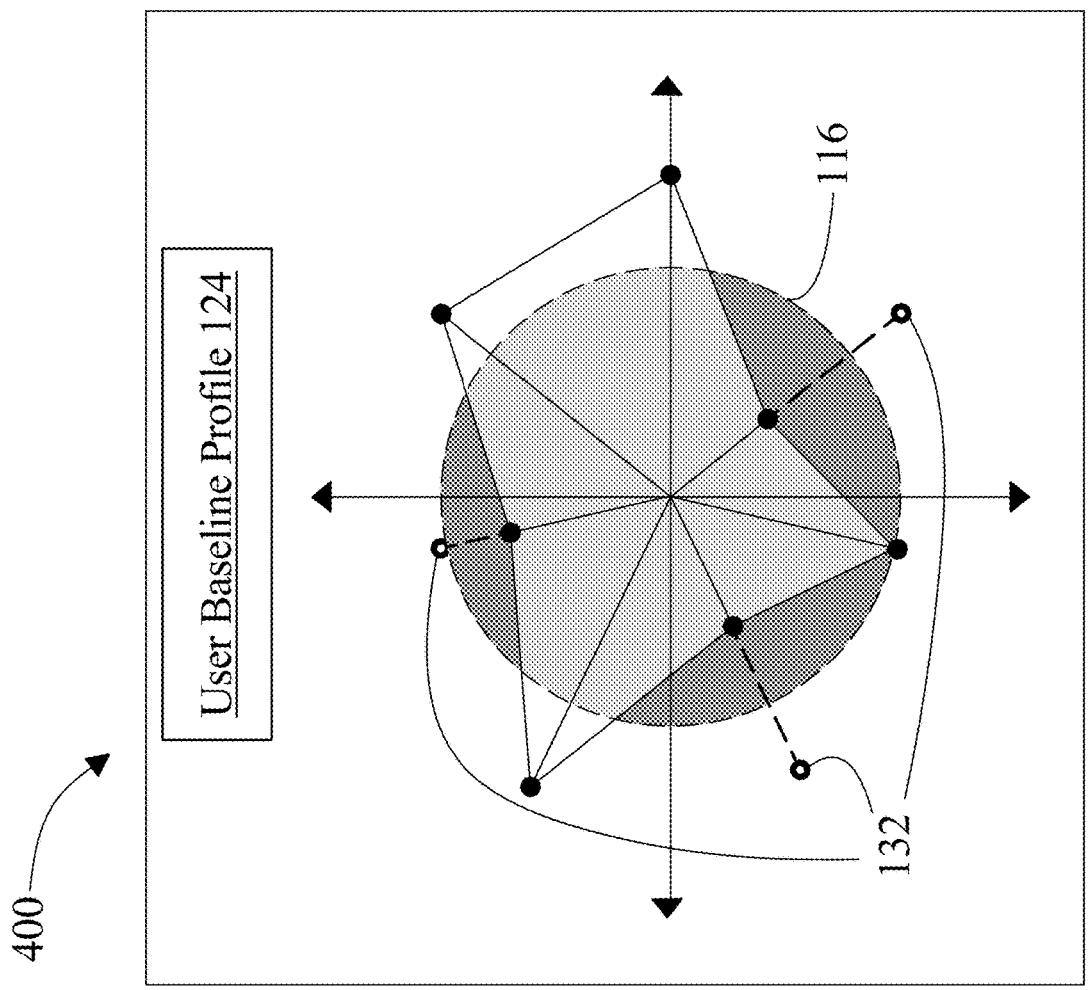
FIG. 4 is a diagrammatic representation of a user baseline profile as a function of the plurality of biological extraction data.

Referring now to FIG. 4, a diagrammatic representation of a user baseline profile 124 as a function of the plurality of biological extraction data 400 is illustrated. In non-limiting illustrative embodiments, a user baseline profile 124 may be illustrated as a series of points, representing polar coordinates, radial vectors, or the like, that correspond to a measure of an element of a plurality of elements that may be included a user baseline profile 124. Elements included in a user baseline profile 124 may be a variety of physiological data regarding, for instance without limitation, sleep duration, frequency, and/or quality; physical fitness, strength, endurance, and/or cardiovascular shape; medical history data including major hospitalizations, diagnoses, surgeries, current medications, BMI, and/or age; blood chemistry data, among other data, as described above. In non-limiting illustrative embodiments, the areas between points, illustrated as the lighter grey shaded spaces, denote the overall user baseline profile 124 as it pertains to having satisfied, achieved, reached, or otherwise addressed elements corresponding to a physiological goal 116, denoted by the black dotted-line circle. In non-limiting illustrative embodiments, the area under the black dotted-line circle, illustrated as the darker grey shaded area, may correspond to regions of the user baseline profile 124 that do not meet a physiological goal 116. In non-limiting illustrative embodiments, differential actions 132 denoted as black radial, dashed-lines and empty circles, may then be determined by a machine-learning process to address deficiencies in a user baseline profile 124 in achieving a goal; the distance of each black radial, dashed-lines to an empty circles may correspond to calculated values, functions, vectors, and the like that contain measured data as to the magnitude, degree, timing, and/or impact that each differential action may have in changing the user baseline profile 124 towards achieving a physiological goal 116.

Continuing in reference to FIG. 1, computing device 104 may be configured to generate plurality of candidate differential actions 132 by generating a ranked-score list of candidate differential actions 132 as a function of a physiological goal 116 and a user baseline profile 124. Generating a ranked-score list may include weighting a plurality of candidate actions as a function of a physiological goal 116 and a user baseline profile 124, and then ranking accordingly. Computing device 104 may weight candidate differential actions 132 using a first optimization process 140, as described in further detail below. Weighting differential actions 132 may be performed based upon a scoring function, or the like, using a first optimization process 140. An "optimization process," as described herein refers to optimization performed by one or more 'objective function' used by a computing device 104 to place elements in an optimal listing based upon a score or numerical value, as described in further detail below. A computing device 104 may compute a score associated with each candidate action and select actions to minimize and/or maximize the score, depending on whether an optimal result is represented, respectively, by a minimal and/or maximal score; a mathematical function, described herein as an "objective function," may be used by computing device 104 to score each possible pairing. Objective function may be based on one or more objectives, as described below. Computing device 104 may pair a predicted route, with a given courier, that optimizes objective function. In various embodiments a score of a particular goal may be based on a combination of one or more factors, including user data 116. Each factor may be assigned a score based on predetermined variables. In some embodiments, the assigned scores may be weighted or unweighted, for instance and without limitation as described in the U.S. Nonprovisional application Ser. No. 16/890,686, filed on Jun. 2, 2020, and entitled "ARTIFICIAL INTELLIGENCE METHODS AND SYSTEMS FOR CONSTITUTIONAL ANALYSIS USING OBJECTIVE FUNCTIONS," the entirety of which is incorporated herein by reference.

Optimization of an objective function may include performing a greedy algorithm process. A "greedy algorithm" is defined as an algorithm that selects locally optimal choices, which may or may not generate a globally optimal solution. For instance, computing device 104 may select goals so that scores associated therewith are the best score for each goal. For instance, in non-limiting illustrative example, optimization may determine the combination of routes for a courier such that each delivery pairing includes the highest score possible, and thus the most optimal delivery.

Still referring to FIG. 1, objective function may be formulated as a linear objective function, which computing device 104 may solve using a linear program such as without limitation a mixed-integer program. A "linear program," as used in this disclosure, is a program that optimizes a linear objective function, given at least a constraint. For instance, in non-limiting illustrative examples, a given constraint might be a nutritional deficiency of a user, and a linear program may use a linear objective function to calculate minimized caloric intake for weight loss without exacerbating a nutritional deficiency. In various embodiments, system 100 may determine a set of instructions towards achieving a user's goal that maximizes a total score subject to a constraint that there are other competing goals. A mathematical solver may be implemented to solve for the set of instructions that maximizes scores; mathematical solver may be implemented on computing device 104 and/or another device in system 100, and/or may be implemented on third-party solver.

With continued reference to FIG. 1, optimizing objective function may include minimizing a loss function, where a "loss function" is an expression an output of which an optimization process minimizes to generate an optimal result. As a non-limiting example, computing device 104 may assign variables relating to a set of parameters, which may correspond to score components as described above, calculate an output of mathematical expression using the variables, and select a goal that produces an output having the lowest size, according to a given definition of "size," of the set of outputs representing each of plurality of candidate ingredient combinations; size may, for instance, included absolute value, numerical size, or the like. Selection of different loss functions may result in identification of different potential pairings as generating minimal outputs Weighting a ranked-score list of candidate actions as a function of a physiological goal 116 and a user baseline profile 124 may include using a scoring function to calculate weighting of candidate actions. A scoring function may be stored in and/or retrieved from a user database 300. A scoring function may be used to weight candidate actions on a variety of factors, including without limitation, anticipated versus experienced level of difficulty in executing differential action, tractability of physiological goal, user baseline profile 124 values, severity of physiological issues, among other factors. Weighting of differential actions 132 based on at least a factor may then provide numerical data for generating a ranked-score list to place candidate actions in a logical order based on weights.

Continuing in reference to FIG. 1, weighting a ranked-score list of candidate actions may include using first optimization process 140 to generate a prioritized differential action set 144. First optimization process 140, as described above, may accept an input of a list of candidate differential actions 132 and apply at least a scoring function, or the like, to weight each differential action 132 according to one or more criterion. First optimization process 140 may then rank the candidate set of differential actions 132 into a logical order, for instance and without limitation, a chronological order, a numerically increasing and/or decreasing order, an order based on ease of adoption, etc., based upon the scoring criteria and/or weighting process. First optimization process 140 may then output a prioritized differential action set 144 according to a ranked-score list of actions as they address a physiological goal 116. For instance in non-limiting examples, an first optimization process 140 may input a list of candidate differential actions 132 for addressing a physiological goal 116 of 'improving user body composition within 6 months', and weight the candidate actions based on how easily a user may adopt each differential action 132 based on current user baseline profile 124; the first optimization process 140 may then rank these candidate actions, for instance and without limitation, from easiest to adopt to most difficult to perform to output a ranked-score list of candidate actions that a user may more realistically adhere to accomplish the goal within the 6 month timeframe.

Figure 5:
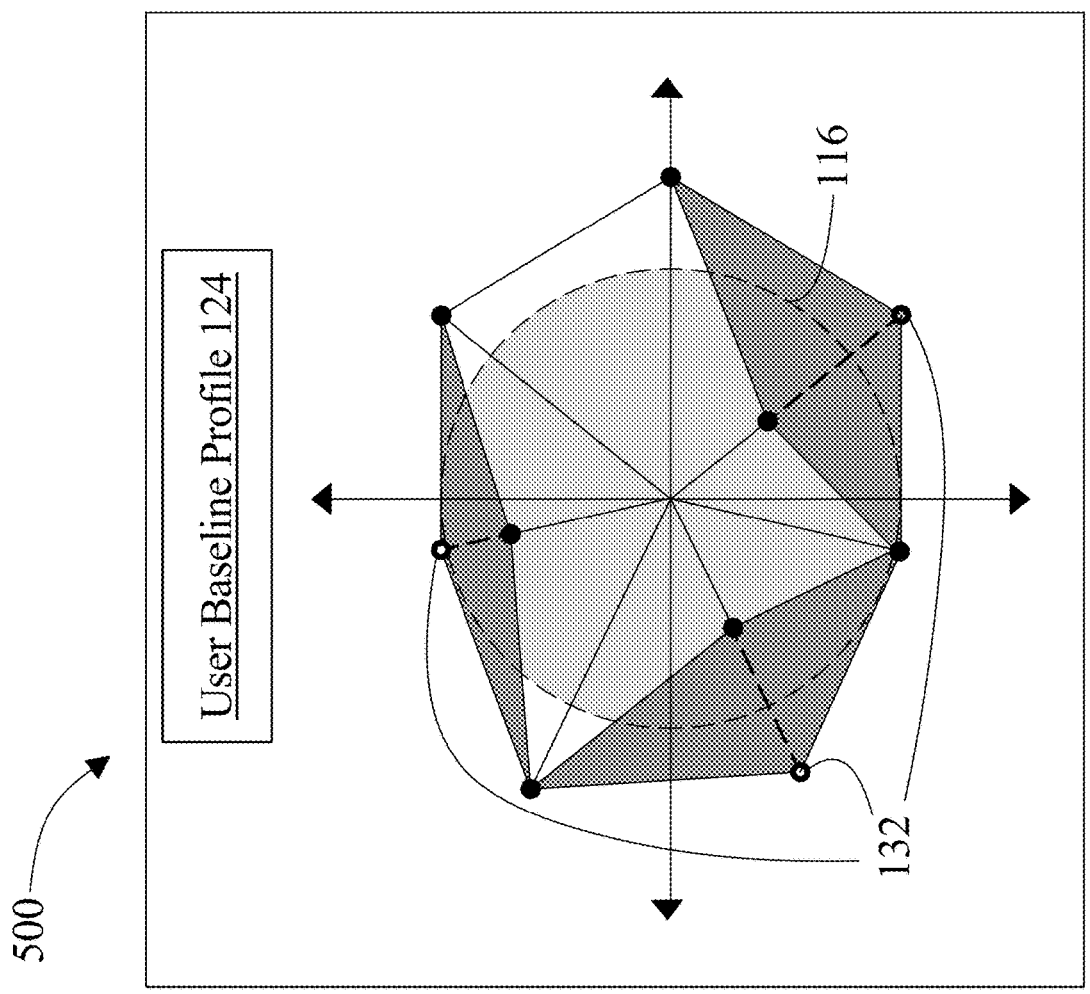
FIG. 5 is a diagrammatic representation of the effect of a plurality of differential actions as a function of a user baseline profile.

Referring now to FIG. 5, a non-limiting exemplary embodiment of a diagrammatic representation of the effect of a plurality of differential actions as a function of a user baseline profile 500 is illustrated. In non-limiting illustrative embodiments, differential actions 132 denoted as black radial, dashed lines and empty circles, may be applied to a user baseline profile 124 to determine progress toward reaching the physiological goal 116 (dashed circle). Completion of a plurality of differential actions 132 may increase the distance of each black radial, dashed-lines to an empty circle, corresponding to calculated values, functions, vectors, and the like that contain measured data as to the magnitude, degree, timing, and/or impact that each differential action 132 may have in changing the user baseline profile 124 towards achieving a physiological goal 116. A machine-learning process may then calculate the new difference between the shaded region once a plurality of differential actions 132 are completed to the region necessary to achieve a physiological goal 116.

Continuing in reference to FIG. 1, computing device 104 may receive a plurality of user preference data 148. User preference data 148 may be input via a user client device 200. User preference data 148 may be prompted after differential actions 132 have been provided to a user and/or weighting of differential actions 132 may be performed as a function of user preference data 148 provided prior to outputting the prioritized differential action set 144. In non-limiting illustrative examples, user preference data 148 may include selecting which differential actions a user prefers, financial considerations, time constraints, user performance difficulty, geolocation data relating to a user resource availability such as to fitness centers, libraries, pools, clinics, grocery stores, and the like, for performing a differential action 132, among other user preference data. User preference data may be used an input data stored and/or retrieved from a user database 200 by a machine-learning process and/or optimization algorithm generating, measuring, weighting, or otherwise outputting a differential action 132.

Figure 6:
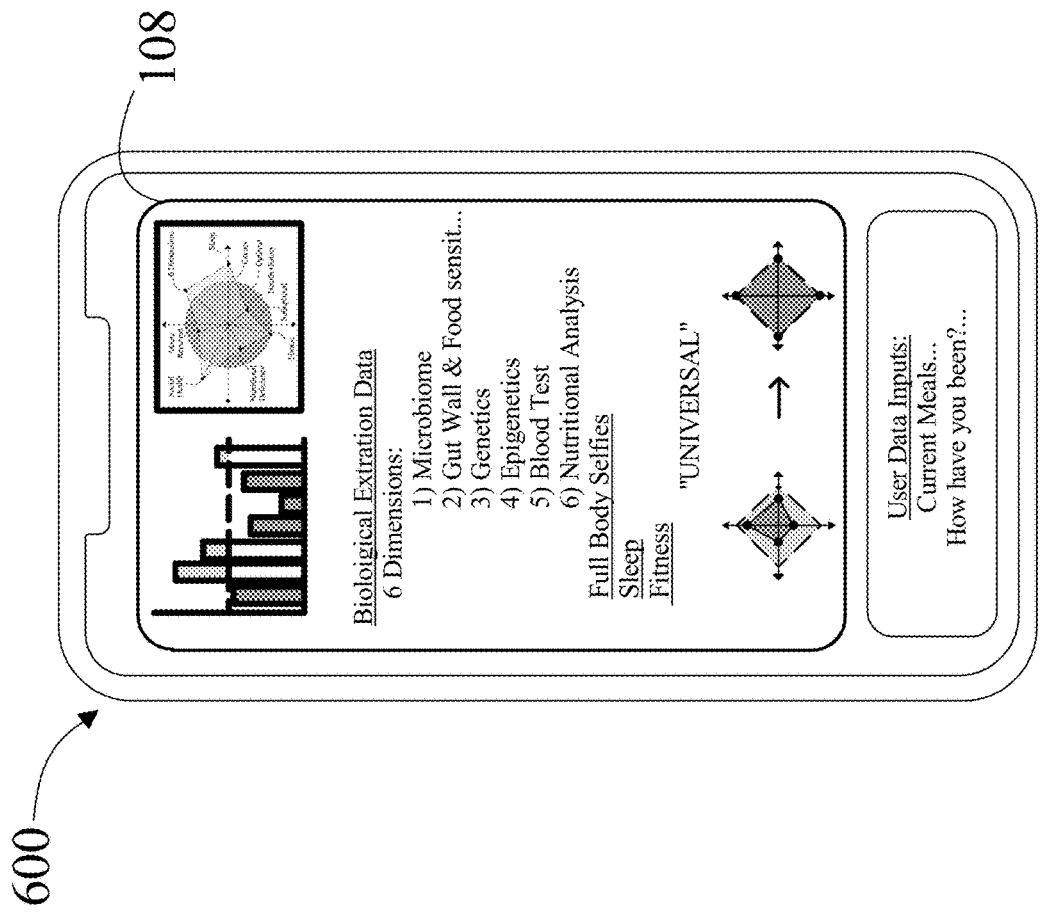
FIG. 6 is a diagrammatic representation of an exemplary embodiment of a user device for providing biological extraction data corresponding to a user

Referring now to FIG. 6, an exemplary embodiment of a user client device 600 for receiving and/or providing a plurality of biological extraction data 108 is illustrated. A computing device 104 may receive and/or provide a plurality of biological extraction data 108 corresponding to the user via a user client device 600, as described in further detail below. Computing device may communicate with a client device, as described in further detail below. User device 600 may display graphical representations of biological extraction data 108, as described in further detail below. User device 600 may provide biological extraction data 108 to via a graphical user interface (GUI), or the like. Persons skilled in the art, upon reviewing the entirety of this disclosure, will be aware of various ways in which graphical displays of biological extraction data 108 may be communicated via a user device 600 to user.

Referring again to FIG. 1, computing device 104 may generate differential action by selecting the differential action 132 from plurality of candidate differential actions 132 as a function of user preference data 148 and at least a physiological goal 116. Selection of differential action 132 may be performed by creating an objective function and then optimizing a selection procedure of an objective function using user preference data 148, physiological goal 116, and/or user baseline profile 124, as previously described. The objective function and/or optimization thereof may be implemented as described above. Alternatively or additionally, selection of a differential action 132 from a plurality of candidate differential actions 132 may be performed by a machine-learning process, as described above.

Continuing in reference to FIG. 1, a computing device 104 may be configured to receive an updated biological extraction datum corresponding to the user, wherein updated biological extraction data 152 may include at least a second element of user data that is more recent in time than a first set of a plurality of biological extraction data 108. Updated biological extraction data 152 may correspond to a user as an update to any element of biological extraction data 108 after adopting at least a differential action 132. Alternatively or additionally, updated biological extraction data may be new biological extraction data 108 that is of a different category than the first biological extraction data 108 used with a physiological goal 116, as described above.

Continuing in reference to FIG. 1, computing device 104 may use updated biological extraction data 152 to generate an updated user baseline profile 156 using a third machine-learning process 160. Third machine-learning process may be implemented in any manner suitable for implementation of first machine-learning process 112. In an embodiment, third machine-learning process 160 may be the same as a first machine-learning process 112. Third machine-learning process 160 may accept an input of at least an element of updated biological extraction data 152 and a first user baseline profile 124 to generate an output of an updated user baseline profile 156, wherein the updated user baseline profile 156 reflects any changes in biological extraction data 108, as described above. Updated user baseline profile 156 may include changes that reflect a user performing at least a differential action 132, changes that indicate a physiological goal 116 was achieved, and/or changes resulting from a new diagnosis, diet, fitness, sleep, physiological change, or the like. In non-limiting illustrative examples, an updated user baseline profile 156 may reflect changes in a user after beginning a new medication, treatment regimen, or the like, wherein the updated user baseline profile 156 indicates that the user may be eligible for new differential actions 132 and/or physiological goals 116.

Referring now to FIG. 6, an exemplary embodiment of a diagrammatic representation of a plurality of differential actions as a function of a user baseline profile 600 is illustrated. In non-limiting illustrative embodiments, an updated user baseline profile 156 after a user performed a plurality of differential actions 132 may be represented as the original user baseline profile 124, with an increase or decrease in parameters (dark grey shaded area) corresponding to a physiological goal 116 (area within dashed circle). In further non-limiting illustrative embodiments, an updated user baseline profile 156 may be represented by the dark-grey shaded area in addition to the original lighter grey area.

Continuing in reference to FIG. 1, a computing device 104 may modify a differential action 132 as a function of the updated biological extraction data 156 using a fourth machine-learning process 164 and at least a more recent element of user data 152. A fourth machine-learning process 164 may be implemented in any manner suitable for implementation of a first machine-learning process 112. The fourth machine-learning process 164 may accept an input of at least a first differential action 132 and/or a plurality of differential actions 132 and an updated user baseline profile 156 to generate an output of at least an updated differential action 168 as a function of any changes from the updated biological extraction data 152. In non-limiting illustrative examples, an updated differential action 168 may describe a new course of action that resulted from completion, redundancy, and/or elimination of an earlier differential action 132 due to any changes in biological extraction data 108 and/or user preference data 148 reflected in the updated user baseline profile 156. An updated differential action 168 may include a course of action for a user in achieving a first physiological goal 116, a new physiological goal 116, and/or may supplant, be identical to, or be different than a previous differential action 132.

Continuing in reference to FIG. 1, computing device 104 may modify differential action 132 by weighting a new ranked-score list of candidate actions as a function of a physiological goal 116 and the updated user baseline profile 156. A second optimization process 172 may be used to weight at least an updated differential action 168 using a scoring function, and place a plurality updated differential actions 164 into a ranked-score list in a logical order. A second optimization process 172 may be implemented like a first optimization process 140. A logical order may be a chronological ordering, an ascending and/or descending order by step in achieving a desired outcome, an order based upon health impact, severity, or the like, as previously described with a first optimization process 140. A second optimization process 172 may be the same as a first optimization process 140. The second optimization process 172 may weight a list of updated differential actions 164 and/or a first differential action 132, as described above with a first optimization process 140, resulting in an updated ranked-score list of candidate actions 176.

Referring back to FIG. 1, computing device 104 may generate a new prioritized differential action set 180 by calculating an anticipated level of difficulty in achieving a goal for user. Anticipated level of difficulty of an action of an updated ranked-score list of candidate actions 176 may be represented by a numerical value, function, vector, coordinates, or the like, for instance and without limitation, that functions as a signifier matching at least an action and/or an updated differential action 168 to an anticipated level of difficulty. Anticipated level of difficulty may be a signifier that is a quantitative and/or qualitative determination stored and/or retrieved from a database, such as a user database 300, by a machine-learning process and/or optimization process. Alternatively or additionally anticipated level of difficulty may be determined from a variety of factors, for instance and without limitation, tractability of a goal, nature of a goal, number of differential actions that can be found to address the goal, and relative ability of a user to perform differential action, and the like, that is calculated by a machine-learning process. The anticipated level of difficulty may be used as a factor for ranking, scoring, and/or otherwise optimizing a list, ranking, or the like, by an optimization process for generating a list of actions. In non-limiting illustrative examples, a fifth machine-learning process may determine an anticipated level of difficulty of a differential action 132 after an optimization process has generated an updated ranked-score list of candidate actions 176 to output a new prioritized differential action set 180. Alternatively or additionally, in non-limiting illustrative examples, a fourth machine-learning process 164 may determine an anticipated level of difficulty for a differential action by determining how a user performed a first differential action 132, for instance and without limitation, the degree to which a differential action was performed and/or the time of completion prior to a second optimization process 172. In further non-limiting examples, a fourth machine-learning process 164 may retrieve from a database a metric that describes the anticipated level of difficulty for a differential action to be performed in accordance to a user baseline profile, for instance indicating age, surgeries, major hospitalizations, diagnoses, underlying medical conditions, and the like. Although these are physiological considerations associated with a user baseline profile, there are non-physiological elements of data that may be used for calculating the anticipated level of difficulty, for instance and without limitation, user preference data, and geolocated resource availability, and the like. Anticipated level of difficulty may be used as a metric, score, weight, or the like, by a second optimization process 172 to output a new prioritized differential action set 180.

Figure 7:
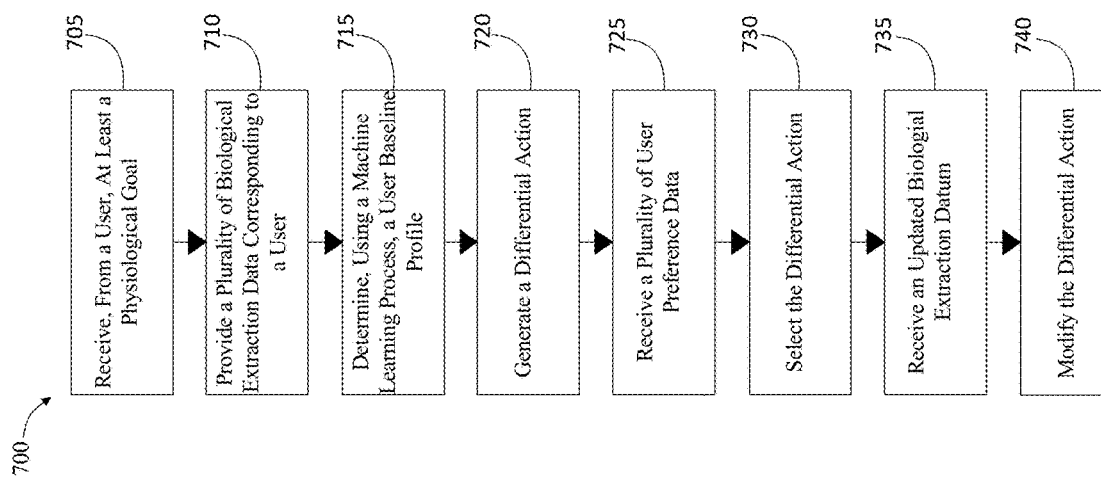
FIG. 7 is a flow diagram illustrating a method of generating rank-ordered instruction sets using an optimization program.

Referring now to FIG. 7, a method of generating rank-ordered instruction sets using an optimization program 700 is illustrated. At step 705, computing device 104 may be designed and configured to receive, from a user, at least a physiological goal 116.

At step 710, a source may provide a plurality of biological extraction data 108 corresponding to the user. A source providing biological extraction data 108 may be a user, a physician, caretaker, database, or any source of user data. Computing device may receive a plurality of biological extraction data 108 corresponding to a user via a user client device 200, retrieve from a user database 300, receive input via a graphical user interface (GUI) from a user, or any other method suitable for providing biological extraction data 108. Persons skilled in the art, upon reviewing the entirety of this disclosure, will be aware of various ways in which biological extraction data 108 may be provided to a computing device from the above sources.

At step 715, computing device 104 may determine, using a machine-learning process, a user baseline profile 124 as a function of the plurality of biological extraction data 108 and the at least a physiological goal 116. Determining a user baseline profile 124 may include using a first machine-learning process 112 and may further include using training data 120 and training the machine-learning process as a function of the training data 120.

At step 720, computing device 104 may generate a differential action 132 as a function of the user baseline profile 124 and the at least a physiological goal 116, wherein generating the differential action 132 may include generating a plurality of candidate differential actions as a function of the user. Generating a differential action 132 may include using a second machine-learning process 136 to calculate a difference between a physiological goal 116 and a user baseline profile 124. Generating a plurality of candidate differential actions 132 may include weighting a ranked-score list of candidate actions as a function of a physiological goal 116 and a user baseline profile 124. Weighting a ranked-score list of candidate actions further comprises using an optimization algorithm to generate a prioritized differential action set.

At step 725, computing device 104 may receive a plurality of user preference data. Computing device 104 may be designed and configured to receive user preference data from a user client device 200, retrieve from a user database 200, among other sources, as described above.

At step 730, computing device 104 may select the differential action 132 from the plurality of candidate differential actions as a function of the user preference data and the at least a physiological goal 116.

At step 735, computing device 104 may receive an updated biological extraction datum corresponding to the user. An updated biological extraction data 108 corresponding to the user may include at least a second element of user data that is more recent in time than a first set of a plurality of biological extraction data 108 corresponding to the user. Computing device 104 may be designed and configured to receive user preference data from a user client device 200, retrieve from a user database 200, among other sources, as described above.

At step 740, computing device 104 may modify the differential action 132 as a function of the updated biological extraction datum. Modifying the differential action 132 as a function of the updated biological extraction datum may include using a second machine-learning process 136 with a first set of differential actions 132 and at least a more recent element of user data, and generating a second differential action 132. Generating a second differential action 132 may include using a machine-learning algorithm to match user data and goal criteria to determine if a goal was met. Modifying the differential action 132 as a function of the updated biological extraction datum may include generating a new user baseline with the updated user data, weighting a new ranked-score list of candidate actions as a function of a physiological goal and the updated user baseline profile, and generating a new prioritized differential action set. Generating a new prioritized differential action set 172 further comprises calculating the anticipated level of difficulty in achieving a goal for the user as a function of the updated biological extraction datum, as described above.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 8:
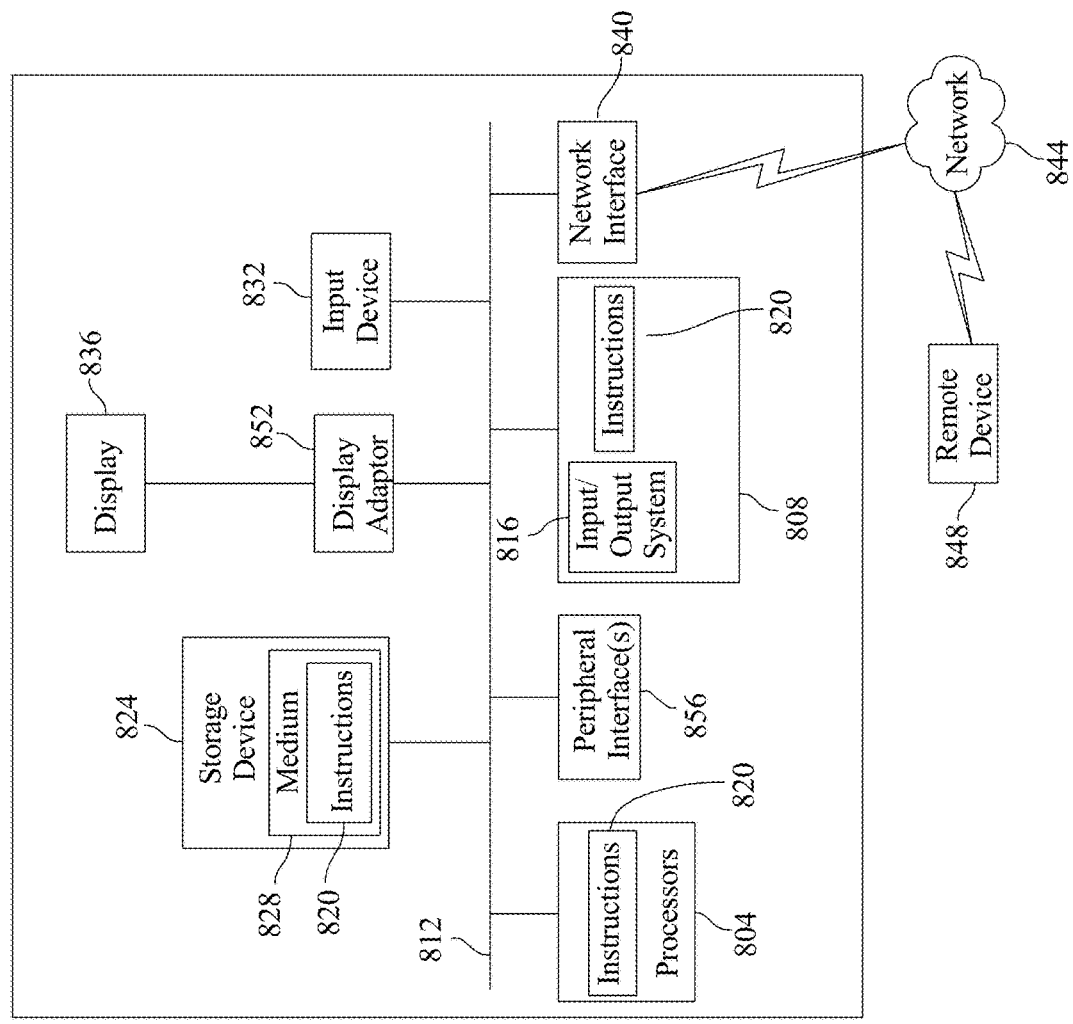
FIG. 8 is a block diagram of a computing system that can be used to implement any one or more of the methodologies disclosed herein and any one or more portions thereof.

FIG. 8 shows a diagrammatic representation of one embodiment of a computing device in the exemplary form of a computer system 800 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 800 includes a processor 804 and a memory 808 that communicate with each other, and with other components, via a bus 812. Bus 812 may include any of several types of bus structures including, but not limited to, a memory bus, a memory controller, a peripheral bus, a local bus, and any combinations thereof, using any of a variety of bus architectures.

Processor 804 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 804 may be organized according to Von Neumann and/or Harvard architecture as a non-limiting example. Processor 804 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC)

Memory 808 may include various components (e.g., machine-readable media) including, but not limited to, a random-access memory component, a read only component, and any combinations thereof. In one example, a basic input/output system 816 (BIOS), including basic routines that help to transfer information between elements within computer system 800, such as during start-up, may be stored in memory 808. Memory 808 may also include (e.g., stored on one or more machine-readable media) instructions (e.g., software) 820 embodying any one or more of the aspects and/or methodologies of the present disclosure. In another example, memory 808 may further include any number of program modules including, but not limited to, an operating system, one or more application programs, other program modules, program data, and any combinations thereof.

Computer system 800 may also include a storage device 824. Examples of a storage device (e.g., storage device 824) include, but are not limited to, a hard disk drive, a magnetic disk drive, an optical disc drive in combination with an optical medium, a solid-state memory device, and any combinations thereof. Storage device 824 may be connected to bus 812 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 824 (or one or more components thereof) may be removably interfaced with computer system 800 (e.g., via an external port connector (not shown)). Particularly, storage device 824 and an associated machine-readable medium 828 may provide nonvolatile and/or volatile storage of machine-readable instructions, data structures, program modules, and/or other data for computer system 800. In one example, software 820 may reside, completely or partially, within machine-readable medium 828. In another example, software 820 may reside, completely or partially, within processor 804.

Computer system 800 may also include an input device 832. In one example, a user of computer system 800 may enter commands and/or other information into computer system 800 via input device 832. Examples of an input device 832 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 832 may be interfaced to bus 812 via any of a variety of interfaces (not shown) including, but not limited to, a serial interface, a parallel interface, a game port, a USB interface, a FIREWIRE interface, a direct interface to bus 812, and any combinations thereof. Input device 832 may include a touch screen interface that may be a part of or separate from display 836, discussed further below. Input device 832 may be utilized as a user selection device for selecting one or more graphical representations in a graphical interface as described above.

A user may also input commands and/or other information to computer system 800 via storage device 824 (e.g., a removable disk drive, a flash drive, etc.) and/or network interface device 840. A network interface device, such as network interface device 840, may be utilized for connecting computer system 800 to one or more of a variety of networks, such as network 844, and one or more remote devices 848 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 844, may employ a wired and/or a wireless mode of communication. In general, any network topology may be used. Information (e.g., data, software 820, etc.) may be communicated to and/or from computer system 800 via network interface device 840.

Computer system 800 may further include a video display adapter 852 for communicating a displayable image to a display device, such as display device 836. Examples of a display device include, but are not limited to, a liquid crystal display (LCD), a cathode ray tube (CRT), a plasma display, a light emitting diode (LED) display, and any combinations thereof. Display adapter 852 and display device 836 may be utilized in combination with processor 804 to provide graphical representations of aspects of the present disclosure. In addition to a display device, computer system 800 may include one or more other peripheral output devices including, but not limited to, an audio speaker, a printer, and any combinations thereof. Such peripheral output devices may be connected to bus 812 via a peripheral interface 856. Examples of a peripheral interface include, but are not limited to, a serial port, a USB connection, a FIREWIRE connection, a parallel connection, and any combinations thereof The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for determining a prioritized instruction set for a user, the system comprising a computing device, wherein the computing device is designed and configured to:
receive, from a user, at least a physiological goal;
provide a plurality of biological extraction data corresponding to the user;
determine a user baseline profile, wherein determining the user baseline profile further comprises:
receiving training data, wherein the training data comprises input data and output data, wherein the input data comprises biological extraction data elements and physiological goals data elements, and user baseline profile output data elements;
categorizing the training data as a function of a natural language machine learning process, wherein categorizing the training data comprises detecting correlations of the biological extraction data elements and the physiological goals data elements to the baseline profile data elements;
training the machine-learning model as a function of the categorized training data; and
determining, using the trained machine-learning model, the user baseline profile as a function the plurality of biological extraction data and the at least a physiological goal;
generate a differential action as a function of the user baseline profile and the at least a physiological goal, wherein generating the differential action further comprises:
generating a plurality of candidate differential actions as a function of the user baseline profile and the physiological goal;
receiving a plurality of user preference data; and
selecting the differential action from the plurality of candidate differential actions as a function of the user preference data and the at least a physiological goal, wherein selecting the differential action comprises:
creating an objective function; and
optimizing a selection procedure of the objective function as a function of the user preference data, the at least a physiological goal and the user baseline profile;
receive an updated biological extraction datum corresponding to the user; and
modify the differential action as a function of the updated biological extraction datum.

2. The system of claim 1, wherein determining the user baseline profile further comprises using a first machine-learning process to determine a correlation between the plurality of biological extraction data corresponding to the user and the at least a physiological goal.

3. The system of claim 1, wherein generating the plurality of differential action candidates further comprises:
using a second machine-learning process to calculate a difference between the at least a physiological goal and the user baseline profile; and
retrieving, from a database, a candidate differential action to address the difference between the at least a physiological goal and the user baseline profile.

4. The system of claim 3, wherein generating the plurality of candidate differential actions further comprises generating a ranked-score list of candidate differential actions as a function of the at least a physiological goal and the user baseline profile.

5. The system of claim 4, wherein generating a ranked-score list of candidate actions further comprises using a first optimization process to generate a prioritized differential action set.

6. The system of claim 1, wherein the updated biological extraction data further comprises at least a second element of user data that is more recent in time than the plurality of biological extraction data.

7. The system of claim 6, wherein modifying the differential action as a function of the updated biological extraction datum further comprises:
using a third machine-learning process with the user baseline profile and the second element of user data; and
generating, as a function of the more recent user data and the user baseline profile, an updated user baseline profile.

8. The system of claim 7, wherein modifying the differential action as a function of the updated biological extraction datum further comprises generating a second plurality of differential actions comprising:
using a fourth machine-learning process to calculate a difference between a physiological goal and the updated user baseline profile; and
retrieving, from a database, a candidate differential action to address the difference between the at least a physiological goal and the user baseline profile.

9. The system of claim 7, wherein modifying the differential action as a function of the updated biological extraction datum further comprises:
generating a new user baseline with the updated user data;
weighting a new ranked-score list of candidate actions as a function of the at least a physiological goal and the updated user baseline profile; and
generating a new prioritized differential action set.

10. The system of claim 9, wherein generating a new prioritized differential action set further comprises:
calculating an anticipated level of difficulty in achieving the physiological goal for the user as a function of the updated biological extraction datum; and
generating the prioritized differential action set as a function of calculated anticipated difficulty.

11. A method for determining a prioritized instruction set for a user, the method comprising a computing device, wherein the computing device is designed and configured for:
receiving, from a user, at least a physiological goal;
providing a plurality of biological extraction data corresponding to the user;
determining a user baseline profile, wherein determining the user baseline profile further comprises:
receiving training data, wherein the training data comprises input data and output data, wherein the input data comprises biological extraction data elements and physiological goals data elements, and user baseline profile output data elements;
categorizing the training data as a function of a natural language machine learning process, wherein categorizing the training data comprises detecting correlations of the biological extraction data elements and the physiological goals data elements to the baseline profile data elements;

training the machine-learning model as a function of the categorized training data; and determining, using the trained machine-learning model, the user baseline profile as a function the plurality of biological extraction data and the at least a physiological goal;

generate a differential action as a function of the user baseline profile and the at least a physiological goal, wherein generating the differential action further comprises:

generating a plurality of candidate differential actions as a function of the user baseline profile and the physiological goal;

receiving a plurality of user preference data; and selecting the differential action from the plurality of candidate differential actions as a function of the user preference data and the at least a physiological goal, wherein selecting the differential action comprises:

creating an objective function; and optimizing a selection procedure of the objective function as a function of the user preference data, the at least a physiological goal and the user baseline profile;

receive an updated biological extraction datum corresponding to the user; and modify the differential action as a function of the updated biological extraction datum.

12. The method of claim 11, wherein determining the user baseline profile further comprises using a first machine-learning process to determine a correlation between the plurality of biological extraction data corresponding to the user and the at least a physiological goal.

13. The method of claim 11, wherein generating the plurality of differential action candidates further comprises:

using a second machine-learning process to calculate a difference between the at least a physiological goal and the user baseline profile; and retrieving, from a database, a candidate differential action to address a difference between the at least a physiological goal and the user baseline profile.

14. The method of claim 13, wherein generating the plurality of candidate differential actions further comprises generating a ranked-score list of candidate differential actions as a function of a physiological goal and the user baseline profile.

15. The method of claim 14, wherein generating a ranked-score list of candidate actions further comprises using a first optimization process to generate a prioritized differential action set.

16. The method of claim 11, wherein the updated biological extraction data further comprises at least a second element of user data that is more recent in time than the plurality of biological extraction data.

17. The method of claim 16, wherein modifying the differential action as a function of the updated biological extraction datum further comprises:

using a third machine-learning process with the user baseline profile and the second element of user data; and generating, as a function of the more recent user data and the user baseline profile, an updated user baseline profile.

18. The method of claim 17, wherein modifying the differential action as a function of the updated biological extraction datum further comprises generating a second plurality of differential actions comprising:

using a fourth machine-learning process to calculate a difference between the at least a physiological goal and the updated user baseline profile; and retrieving, from a database, a candidate differential action to address the difference between the at least a physiological goal and the user baseline profile.

19. The method of claim 17, wherein modifying the differential action as a function of the updated biological extraction datum further comprises:

generating a new user baseline with the updated user data;

weighting a new ranked-score list of candidate actions as a function of the at least a physiological goal and the updated user baseline profile; and generating a new prioritized differential action set.

20. The method of claim 19, wherein generating a new prioritized differential action set further comprises:

calculating an anticipated level of difficulty in achieving the physiological goal for the user as a function of the updated biological extraction datum; and generating the prioritized differential action set as a function of the calculated anticipated difficulty.

* * * * *